(12) United States Patent
Junger et al.

(10) Patent No.: US 11,672,475 B2
(45) Date of Patent: **\*Jun. 13, 2023**

(54) COMBINATION TREATMENT USING ELT

(71) Applicant: ELIOS VISION, INC., Los Angeles, CA (US)

(72) Inventors: Johannes Junger, Gilching (DE); Markus Enders, Munich (DE)

(73) Assignee: ELIOS VISION, INC., Los Angeles, CA (US)

(*) Notice: Subject to any disclaimer, the term of this patent is extended or adjusted under 35 U.S.C. 154(b) by 811 days.

This patent is subject to a terminal disclaimer.

(21) Appl. No.: 16/389,446

(22) Filed: Apr. 19, 2019

(65) Prior Publication Data

US 2020/0330266 A1 Oct. 22, 2020

(51) Int. Cl.
*A61F 9/008* (2006.01)
*A61B 5/00* (2006.01)
(Continued)

(52) U.S. Cl.
CPC .............. *A61B 5/4848* (2013.01); *A61B 1/06* (2013.01); *A61F 9/0008* (2013.01); *A61F 9/008* (2013.01);
(Continued)

(58) Field of Classification Search
CPC .. A61F 9/008; A61F 9/00802; A61F 9/00814; A61F 2009/00868;
(Continued)

(56) References Cited

U.S. PATENT DOCUMENTS 4,607,622 A 8/1986 Fritch et al.
4,846,172 A 7/1989 Berlin
(Continued)

FOREIGN PATENT DOCUMENTS

DE 19920615 A1 12/2000
DE 10023176 A1 11/2001
(Continued)

OTHER PUBLICATIONS

Wilmsmerey et al., "Excimer Laser Trabeculotomy—A new, Minimally Invasive Procedure for Patients with Glaucoma," Graefe's Arch for Clin and Exp Ophthalmol (2006), 244: 670-676.*
(Continued)

*Primary Examiner* — Ahmed M Farah
(74) *Attorney, Agent, or Firm* — Greenberg Traurig, LLP; David J. Dykeman; Roman Fayerberg (57) ABSTRACT

A method of treating a subject having glaucoma comprises performing excimer laser trabeculostomy (ELT) on a subject having glaucoma and having previously undergone a failed treatment or a treatment that has been rendered ineffective by progression of the disease. In some examples, the failed treatment is a non-surgical treatment comprising administering medicated eye drops. In some examples, the failed treatment is a laser treatment or surgical treatment, such as a trabeculoplasty, iridotomy, iridectomy, trabeculectomy, trabeculotomy, goniotomy, surgical insertion of a shunt or implant, deep sclerectomy, viscocanalostomy, or a combination thereof.

15 Claims, 8 Drawing Sheets

(51) Int. Cl.
*A61F 9/00* (2006.01)
*A61F 9/009* (2006.01)
*A61B 1/06* (2006.01)
*A61B 17/00* (2006.01)
*A61B 18/22* (2006.01)
*A61B 90/30* (2016.01)

(52) U.S. Cl.
CPC .......... *A61F 9/009* (2013.01); *A61F 9/00814* (2013.01); *A61B 18/22* (2013.01); *A61B 90/30* (2016.02); *A61B 2017/00221* (2013.01); *A61B 2017/00973* (2013.01); *A61F 2009/00868* (2013.01); *A61F 2009/00891* (2013.01)

(58) Field of Classification Search
CPC .......... A61F 2009/00891; A61B 90/30; A61B 2090/306; A61B 2090/308; A61B 2090/309; A61B 18/22
USPC .............. 606/4, 6, 10, 13–15; 600/248, 249; 128/898
See application file for complete search history.

(56) References Cited

U.S. PATENT DOCUMENTS

| | | | |
|---|---|---|---|
| 4,862,888 A | 9/1989 | Yessik | |
| 5,281,241 A | 1/1994 | Patel | |
| 5,323,766 A | 6/1994 | Uram | |
| 5,738,677 A | 4/1998 | Colvard et al. | |
| 5,755,716 A * | 5/1998 | Garito | A61B 18/14 606/49 |
| 5,865,831 A | 2/1999 | Cozean et al. | |
| 6,197,056 B1 | 3/2001 | Schachar | |
| 6,283,974 B1 | 9/2001 | Alexander | |
| 6,514,241 B1 * | 2/2003 | Hsia | A61F 9/00802 606/6 |
| 6,743,221 B1 | 6/2004 | Hobart et al. | |
| 7,443,296 B2 | 10/2008 | Mezhinsky | |
| 7,568,619 B2 | 8/2009 | Todd | |
| 7,801,271 B2 | 9/2010 | Gertner et al. | |
| 9,489,785 B2 | 11/2016 | Klammer | |
| 9,642,746 B2 | 5/2017 | Berlin | |
| 10,383,689 B2 | 8/2019 | Berlin | |
| 11,076,933 B2 | 8/2021 | Junger et al. | |
| 11,076,992 B2 * | 8/2021 | Junger | A61F 9/00802 |
| 11,103,382 B2 | 8/2021 | Junger et al. | |
| 11,234,866 B2 | 2/2022 | Junger et al. | |
| 11,389,239 B2 | 7/2022 | Junger et al. | |
| 11,529,260 B2 | 12/2022 | Junger et al. | |
| 2002/0013572 A1 | 1/2002 | Berlin | |
| 2002/0183726 A1 | 12/2002 | Elbrecht et al. | |
| 2004/0082939 A1 | 4/2004 | Berlin | |
| 2004/0114879 A1 | 6/2004 | Hiereth et al. | |
| 2004/0147985 A1 | 7/2004 | MacFarland et al. | |
| 2005/0192480 A1 | 9/2005 | Toriya et al. | |
| 2005/0283148 A1 | 12/2005 | Janssen | |
| 2006/0111699 A1 | 5/2006 | Neuberger | |
| 2006/0244652 A1 | 11/2006 | Tethrake et al. | |
| 2007/0027443 A1 | 2/2007 | Rose et al. | |
| 2007/0122096 A1 | 5/2007 | Temelkuran et al. | |
| 2007/0147752 A1 | 6/2007 | Weisberg et al. | |
| 2007/0219601 A1 | 9/2007 | Neuberger | |
| 2007/0265602 A1 | 11/2007 | Mordaunt et al. | |
| 2008/0054073 A1 | 3/2008 | Charles | |
| 2008/0082078 A1 * | 4/2008 | Berlin | A61F 9/0017 604/521 |
| 2008/0097415 A1 | 4/2008 | Zimare et al. | |
| 2008/0108981 A1 | 5/2008 | Telfair et al. | |
| 2008/0108983 A1 | 5/2008 | Nadolski | |
| 2008/0161781 A1 | 7/2008 | McArdle et al. | |
| 2008/0269734 A1 | 10/2008 | Vila Echague et al. | |
| 2009/0030300 A1 | 1/2009 | Hhaboussi et al. | |
| 2009/0118715 A1 | 5/2009 | Mansour | |
| 2009/0157064 A1 | 6/2009 | Hodel | |
| 2010/0019125 A1 | 1/2010 | Stefani et al. | |
| 2010/0068141 A1 | 3/2010 | Kaushal et al. | |
| 2010/0324543 A1 | 12/2010 | Kurtz et al. | |
| 2011/0295243 A1 | 12/2011 | Peyman | |
| 2011/0301507 A1 | 12/2011 | Romano et al. | |
| 2012/0275481 A1 | 11/2012 | Riggs | |
| 2013/0041357 A1 | 2/2013 | Neuberger | |
| 2013/0085484 A1 | 4/2013 | Van Valen et al. | |
| 2014/0058367 A1 | 2/2014 | Dantus | |
| 2014/0188096 A1 | 7/2014 | Chia et al. | |
| 2014/0316388 A1 | 10/2014 | Hipsley | |
| 2015/0051607 A1 | 2/2015 | Hajishah et al. | |
| 2015/0080783 A1 | 3/2015 | Berlin | |
| 2015/0148615 A1 | 5/2015 | Brennan et al. | |
| 2015/0217133 A1 | 8/2015 | Angeley et al. | |
| 2015/0297408 A1 | 10/2015 | Dolzan et al. | |
| 2015/0305811 A1 | 10/2015 | Neuberger | |
| 2015/0366706 A1 | 12/2015 | Belkin et al. | |
| 2015/0374549 A1 | 12/2015 | Scott | |
| 2017/0100041 A1 | 4/2017 | Kasamatsu et al. | |
| 2017/0202708 A1 | 7/2017 | Berlin | |
| 2017/0304001 A1 | 10/2017 | Searle et al. | |
| 2018/0000337 A1 | 1/2018 | Chen et al. | |
| 2018/0042772 A1 | 2/2018 | Mansour | |
| 2018/0263647 A1 | 9/2018 | Aljuri et al. | |
| 2018/0303667 A1 | 10/2018 | Peyman | |
| 2018/0353328 A1 | 12/2018 | Bacher et al. | |
| 2018/0360310 A1 | 12/2018 | Berlin | |
| 2019/0105200 A1 | 4/2019 | Hipsley | |
| 2019/0117459 A1 * | 4/2019 | Berlin | A61B 3/13 |
| 2019/0262071 A1 | 8/2019 | Thom et al. | |
| 2020/0078216 A1 | 3/2020 | Raksi | |
| 2020/0078217 A1 * | 3/2020 | Raksi | A61F 9/00825 |
| 2020/0330157 A1 * | 10/2020 | Junger | A61F 9/00781 |
| 2020/0330181 A1 | 10/2020 | Junger et al. | |
| 2020/0330266 A1 | 10/2020 | Junger et al. | |
| 2020/0330274 A1 | 10/2020 | Junger et al. | |
| 2020/0330275 A1 | 10/2020 | Junger et al. | |
| 2020/0330279 A1 | 10/2020 | Junger et al. | |
| 2020/0330280 A1 | 10/2020 | Junger et al. | |
| 2020/0330281 A1 | 10/2020 | Junger et al. | |
| 2020/0390600 A1 * | 12/2020 | Perera | A61B 10/0266 |
| 2021/0235986 A1 | 8/2021 | Juhasz et al. | |
| 2021/0259880 A1 | 8/2021 | Newton et al. | |
| 2021/0298945 A1 * | 9/2021 | Juhasz | G16H 30/40 |
| 2022/0022997 A1 | 1/2022 | Junger et al. | |
| 2022/0023098 A1 | 1/2022 | Junger et al. | |
| 2022/0031513 A1 | 2/2022 | Junger et al. | |
| 2022/0151828 A1 | 5/2022 | Junger et al. | |
| 2022/0183882 A1 | 6/2022 | Mosaed et al. | |
| 2022/0183887 A1 | 6/2022 | Junger et al. | |
| 2022/0280343 A1 | 9/2022 | Junger et al. | |
| 2022/0387107 A1 | 12/2022 | Junger et al. | |
| 2022/0387218 A1 | 12/2022 | Junger et al. | |

FOREIGN PATENT DOCUMENTS

| | | |
|---|---|---|
| DE | 10138984 A1 | 3/2003 |
| EP | 1835862 B1 | 6/2011 |
| EP | 2120760 B1 | 9/2015 |
| WO | 2019060756 A1 | 3/2019 |
| WO | 2020215062 A1 | 10/2020 |
| WO | 2020215064 A1 | 10/2020 |
| WO | 2020215066 A1 | 10/2020 |
| WO | 2020215067 A1 | 10/2020 |
| WO | 2020215068 A1 | 10/2020 |
| WO | 2020215069 A1 | 10/2020 |
| WO | 2020215071 A1 | 10/2020 |
| WO | 2020215073 A1 | 10/2020 |

OTHER PUBLICATIONS

International Search Report and Written Opinion issued in International Application No. PCT/US2020/028970, dated Jul. 5, 2020, 10 pages.

Crandall, Alan, "Combining Cataract and Glaucoma Surgery", Review of Ophthalmology, 1-4, Jun. 13, 2008.

(56) References Cited

OTHER PUBLICATIONS

Craver, Davinder S. "When You Have Cataracts and Glaucoma", Glaucoma Research Foundation, Oct. 29, 2017.
Tsai, James C. "High Eye Pressure and Glaucoma", Glaucoma Research Foundation, Oct. 29, 2017.
Leung et al. "Anterior Chamber Angle Measurement with Anterior Segment Optical Coherence Tomography: a Comparison between Slit Lamp OCT and Visante OCT" IOVS, Aug. 2008, 3469-3474 (Year: 2008).
Taliaferro, Kevin et al. "Excimer Laser Trabeculostomy Normalizing IOP and Restoring Physiologic Outflow in Glaucoma." Glaucoma Today, 2009, pp. 45-47 (Year: 2009).
Toteberg-Harms, et al., "Cataract surgery combined with excimer laser trabeculotomy to lower intraocular pressure: effectiveness dependent on preoperative IOP." BMC ophthalmology, vol. 13, No. 1, p. 24 (2013).
U.S. Appl. No. 16/389,404 US20200330275A1, filed Apr. 19, 2019 Oct. 22, 2020, Combination Treatment Using Phaco and ELT.
U.S. Appl. No. 16/389,437 US20200330281A1, filed Apr. 19, 2019 Oct. 22, 2020, Excimer Laser Fiber Illumination.
U.S. Appl. No. 16/389,346 US20200330181A1, filed Apr. 19, 2019 Oct. 22, 2020, Authentication Systems and Methods for an Excimer Laser System.
U.S. Appl. No. 16/389,359 US20200330279A1, filed Apr. 19, 2019 Oct. 22, 2020, Calibration System for Improving Manufacture Tolerance in Excimer Laser Optical Fibers.
U.S. Appl. No. 16/389,460 US20200330274A1, filed Apr. 19, 2019 Oct. 22, 2020, Methods of Transverse Placement in ELT.
U.S. Appl. No. 16/389,425 US20200330280A1, filed Apr. 19, 2019 Oct. 22, 2020, Personalization of Excimer Laser Fibers.
U.S. Appl. No. 16/389,386 US20200330157A1, filed Apr. 19, 2019 Oct. 22, 2020, Enhances Fiber Probes for ELT.
Berlin et al., "Excimer Laser Trabeculostomy: an Effective Microinvasive Glaucoma Surgery Procedure for Open-Angle Glaucoma", published Dec. 19, 2013 Third Party Submission in 010503.
Dietlein et al., "Erbium: YAG Laser Trabecular Ablation (LTA) in the Surgical Treatment of Glaucoma", Lasers in Surgery and Medicine, Jan. 6, 1999, vol. 23, pp. 104-110.
ExTra Operating Instructions, Manufacturer: Mlase AG, published prior to Jan. 1, 2018.
Francis et al., "Combined Cataract Extraction and Trabeculotomy by the Internal Approach for Coexisting Cataract and Open-Angle Glaucoma: Initial Results", Journal of Cataract & Refractive Surgery, Jul. 1, 2008, vol. 34, pp. 1096-1103.
Investigation Testing Authorization Application, TUI Laser AG, Published Jan. 1, 2016.
Wilmsmeyer et al., "Excimer Laser Trabeculotomy: a New, Minimally Invasive Procedure for Patients With Glaucoma", Graefe's Archive for Clinical and Experimental Ophthalmology, Oct. 19, 2005, vol. 244, pp. 670-676.

\* cited by examiner

COMBINATION TREATMENT USING ELT

TECHNICAL FIELD

The invention relates generally to combined methods for treating glaucoma including excimer laser trabeculostomy (ELT).

BACKGROUND

In glaucoma, there is a build-up of fluid known as aqueous humor in the anterior chamber of the eye. The fluid normally drains from the eye in an area known as the trabecular meshwork, typically flowing through Schlemm's canal in the trabecular meshwork. However, when an individual suffers from glaucoma, the fluid build-up causes elevated intraocular pressure (TOP). The increased pressure gradually leads to damage of the optic nerve and causes irreversible vision loss.

Traditional methods of treating glaucoma manage the condition by decreasing the IOP or producing less aqueous humor. Traditional glaucoma treatment includes pharmaceutical treatments, laser treatments, surgical treatments, and combinations thereof. Pharmaceutical treatments do not provide a permanent solution and instead manage the condition by decreasing production of the fluid or increasing drainage of the fluid to lower IOP. Laser treatments are also used to reduce the IOP by increasing fluid outflow or decreasing fluid production. However, laser and pharmaceutical treatments often are not effective in treating advanced stages of glaucoma. Thus, individuals suffering from glaucoma are also treated by surgical procedures, such as inserting an implant into the eye to increase drainage. However, these procedures are accompanied by risks, such as dislodgment of the implant.

SUMMARY

The invention provides methods for combined treatment of glaucoma using excimer laser trabeculostomy (ELT). Methods include performing ELT on a subject having glaucoma who has previously undergone a failed treatment. Because glaucoma is a progressive disease, previous treatments may be rendered ineffective as the condition worsens. Therefore, glaucoma patients often endure several failed treatments. Methods of the invention provide treatment of glaucoma using ELT and can be implemented even when previous treatment methods have failed. During the ELT procedure, a laser probe is positioned transverse to the Schlemm's canal to create perforations the trabecular meshwork and/or Schlemm's canal to immediately improve fluid drainage. The perforations can also increase outflow of aqueous humor and reduce pressure in the eye.

In examples of the invention, the failed treatment is a traditional method of treating glaucoma, such as a prescribed medication or pharmaceutical treatment, laser treatment, surgical treatment, or combinations thereof. Typically, a prescribed medication or pharmaceutical treatment is a medicated eye drop, such as alpha agonists, beta blockers, carbonic anhydrase inhibitors, cholinergic agonists, prostaglandin/prostamide analogues, or combinations thereof. Examples of laser treatments include trabeculoplasty, iridotomy, iridectomy, and combinations thereof. Examples of trabeculoplasty include argon laser trabeculoplasty (ALT) and selective laser trabeculoplasty (SLT). Surgery is a traditionally a procedure of last resort after medical and laser therapies, due to relatively high complication rates and unpredictability of procedures such as trabeculectomies. Examples of surgical treatment include insertion of a shunt or implant, trabeculectomy, trabeculotomy, goniotomy, deep sclerectomy, viscocanalostomy, or combinations thereof.

An example of the invention is directed to providing glaucoma treatment to a subject who has been administered previous glaucoma treatments that have failed or have been rendered ineffective. For example, a pharmaceutical treatment may have been previously effective in treating the subject's glaucoma before the disease progressed to a state where the pharmaceutical treatment was rendered ineffective. The subject may have undergone a laser treatment, such as selective laser trabeculoplasty (SLT), for treatment of the glaucoma. SLT may have been effective in treating the glaucoma until the condition worsened. Methods of the invention provide ELT as a treatment after the previously-administered treatments have failed or have been rendered ineffective, allowing for drainage of the fluid build-up in the anterior chamber.

In an example of the invention, a subject with advanced glaucoma was administered a prescription medication until the prescription was ineffective, SLT as a laser therapy until the SLT was ineffective, and implant of a stent, which has since become dislodged. Because the subject has advanced glaucoma, treatment methods such as pharmaceutical or existing laser therapy may not be effective in treating the condition. Moreover, because the surgical treatment resulted in a failed stent placement, the stent is not draining the build-up of aqueous humor in the anterior chamber of the eye. By providing ELT treatment according to methods of the invention, perforations are created in the trabecular meshwork and/or Schlemm's canal, and the aqueous humor is allowed to drain. Thus, methods of the invention are effective in draining the fluid build-up, even when previous treatments have failed.

In some embodiments, one or more previous treatments remain effective. In such instances, ELT is administered to provide combination treatment of glaucoma. Providing ELT in addition to other effective treatments creates increased drainage of the aqueous humor from the anterior chamber of the eye. For example, a subject having glaucoma that has undergone one failed treatment method, such as a pharmaceutical treatment, may be administered ELT and SLT as combination therapy. In some instances, such a combined treatment may be administered to the patient during the same surgical visit.

During the ELT procedure of the invention, a physician guides a delivery tip of a fiber probe through a corneal incision in the eye and towards the trabecular meshwork. In some examples, methods of the invention further comprise administering anesthesia to the subject before making the incision and inserting the probe. Typically, the incision has a length of about ⅛ inch or smaller. In some examples, one or more sutures are used to close the incision after ELT treatment. The delivery tip is guided by the physician to a position transverse to the Schlemm's canal to create permanent perforations the trabecular meshwork and/or Schlemm's canal. Fluid drainage in the anterior chamber of the eye is immediately improved by the perforations created in Schlemm's canal and/or the meshwork by the excimer laser. The perforations can also increase outflow of aqueous humor and reduce pressure in the eye. In some cases, the physician uses a Gonio lens, endoscope, or other illumination source to aid in positioning the delivery tip of the fiber probe. Typically, a physician will use a gonio lens to intraoperatively observe a slight reflux hemorrhage as a quality criterion, thereby allowing effective positioning of the fiber at the trabecular meshwork to create a passageway into Schlemm's canal. A further quality criterion is minor reflux bleeding that can be observed intraoperatively, thus allowing effective positioning of the fiber at the trabecular meshwork to open Schlemm's canal.

Once the delivery tip is at a position transverse to the Schlemm's canal, a series of shots of laser energy are delivered to the trabecular meshwork. In an example of the invention, a 308-nm xenon-chloride ultraviolet excimer laser is used in methods of the invention. The 308-nm xenon-chloride ultraviolet excimer laser causes minimal thermal damage compared with visible or infrared lasers. In some examples, the excimer laser is an encapsulated xenon chloride (XeCl) excimer laser such as the EXTRA LASER manufactured by MLase AG. Unlike argon and selective laser trabeculoplasty, ELT precisely excises tissue without causing thermal injury or scarring the surrounding tissue. Because ELT is a non-thermal procedure, tissue reactions in the trabecular meshwork are not shown or activated postoperatively. The lack of heat generation in ELT allows for a nearly absent activation of postoperative tissue reactions and provides long-term stability of the pressure-reducing effects.

Moreover, to avoid the corneal absorption of laser radiation, an optical fiber is used to deliver the energy. The delivery tip of the fiber probe comprises the optical fiber jacketed in metal, such as stainless steel. In some examples of the invention, the delivery tip is beveled (e.g., at 0°, 15°, 30°, and 45° with respect to the tip). The fiber probe comprises an optical fiber suitable for UV light that is embedded into a handheld laser applicator. For example, a FIDO LASER APPLICATOR manufactured by MLase AG may be used as the fiber probe.

To achieve easier drainage of the aqueous humor, which leads to reduced IOP, a total of about 10 ELT sites or perforations, each with about a 200 µm diameter, are lasered into the trabecular meshwork and/or Schlemm's canal. In an example, about 10 shots from excimer laser source are applied to each eye. In some examples, greater than about 10 shots are applied to each eye. In comparison, stents and implants have smaller individual diameters that are between about 80 µm to about 120 µm.

In some embodiments, the patient is administered an anesthetic before surgery. In some examples, the anesthesia is topical. In some examples, the anesthesia comprises anesthetic drops. In some instances, general anesthesia is administered to the patient. The eye is anesthetized first with eye drops and then an injection of anesthetic is administered around the eye. The anesthetic injection itself may cause some mild discomfort; a slight sensation of pressure as the anesthetic is delivered. The injection anesthetizes the eye, preventing not only pain but also excessive eye movement during surgery.

DETAILED DESCRIPTION

Methods of the invention provide treatment of glaucoma using ELT after previously-administered treatments have failed or been rendered ineffective. Previous treatment methods include pharmaceutical treatments, laser treatments, surgical treatments, or combinations thereof. For example, a patient may have previously been prescribed medicated eye drops and may have undergone a selective laser trabeculoplasty (SLT) procedure, but the patient's condition has progressed to a point where those treatments are no longer effective. The invention provides methods of treating the patient by administering ELT treatment to the glaucoma patient who has previously undergone failed treatments.

In examples of the invention, the failed treatment is a prescribed medication or pharmaceutical treatment, laser treatment, surgical treatment, or combination thereof. Traditional methods for treating glaucoma include medicated drops, laser treatment, and surgical treatment. Surgery is a traditionally a procedure of last resort after medical and laser therapies, due to relatively high complication rates and unpredictability of procedures such as trabeculectomies.

Typically, a prescribed medication or pharmaceutical treatment is a medicated eye drop, such as alpha agonists, beta blockers, carbonic anhydrase inhibitors, cholinergic agonists, prostaglandin/prostamide analogues, or combinations thereof. Examples of laser treatments include trabeculoplasty, iridotomy, iridectomy, and combinations thereof. Examples of trabeculoplasty include argon laser trabeculoplasty (ALT) and selective laser trabeculoplasty (SLT). Examples of surgical treatment include insertion of a shunt or implant, trabeculectomy, trabeculotomy, goniotomy, deep sclerectomy, viscocanalostomy, or combinations thereof.

Medication is the most common early treatment for glaucoma, and pharmaceutical options include medicated eye drops, pills, or both. All medications available for the treatment of glaucoma must be taken regularly. Examples of the medicated eye drops include alpha agonists, beta blockers, carbonic anhydrase inhibitors, cholinergic agonists, and prostaglandin/prostamide analogues.

Alpha agonists, such as apraclondine and brimonidine, are used to reduce the production of fluid in the eye and to improve the flow of fluid out of the eye. The drops are typically used two or three times a day. Apraclonidine is for short-term use following laser treatment or to delay laser treatment. Brimonidine is licensed for the long-term treatment of glaucoma, but is contra-indicated for children under the age of two years. Side effects include a dry mouth, tiredness, and general weakness. Patients may develop a severe allergic reaction to the drops, causing the eye to become increasingly red, sore, and sticky. Alpha agonists include formulations of brimonidine (ALPHAGAN manufactured by Allergan, Inc.).

Beta blockers include betaxolol, carteolol, levobunolol, and timolol, and are used to reduce the production of fluid in the eye. The drops are used once or twice a day and are not typically prescribed for anyone susceptible to chest or breathing problems. Side-effects include slow pulse, dizziness, asthma, tiredness, depression, loss of libido, and impotence. Beta adrenergic blocking drops include timolol (TIMOPTIC manufactured by Bausch and Lomb and BETIMOL manufactured by Akorn, Inc.), levobunolol (BETAGAN manufactured by Allergan, Inc.), betaxolol (BETOPTIC manufactured by Alcon Laboratories Inc.), carteolol (OCUPRESS manufactured by Bausch and Lomb Pharmaceuticals Inc.), and metipranolol (OPTIPRANOLOL manufactured by Bausch & Lomb Pharmaceuticals, Inc.).

Carbonic anhydrase inhibitors, such as brinzolamide and dorzolamide, reduce production of fluid in the eye. The drops are used two or three times a day on their own, or twice a day if with another drop. Side-effects include redness of the eye, crusty eyelashes, fatigue, and a bitter taste in the mouth. The carbonic anhydrase inhibitors include oral agents acetazolamide (DIAMOX SEQUELS manufactured by Teva Pharmaceuticals USA, Inc.) and methazolamide (NEPTAZANE manufactured by Perrigo Company plc, Dublin Ireland) and the eyedrops brinzolamide (AZOPT manufactured by Alcon Laboratories Inc., a Novartis company, Novartis Pharmaceuticals Corporation, USA) and dorzolamide (TRUSOPT manufactured by Santen Pharmaceutical Co., Ltd.).

Cholinergic agonist drops, such as pilocarpine, are used to improve the flow of fluid out of the eye. When using cholinergic agonist drops, the usual fluid flow route is improved. Drops are used three or four times a day. Miotic drops include pilocarpine hydrochloride solution manufactured by Akorn, Inc.

Prostaglandin/prostamide analogues include bimatoprost, latanoprost, tafluprost, and travoprost. The drops are used to improve the fluid flow out of the eye through a different way from the usual one. The drops are used once a day. Side effects include a pink eye that typically improves over a period of time, an iris that darkens in color, longer and darker eyelashes, and darkened skin around the orbit of the eye. Examples of prostanoid FP-receptor (sensitive to prostaglandin F) agonists include latanoprost (XALATAN manufactured by Pfizer Inc.), bimatoprost (LUMIGAN manufactured by Allergan, Inc.), travoprost (TRAVATAN Z manufactured by Novartis Pharmaceuticals Corporation), unoprostone (RESCULA manufactured by Sucampo Pharma Americas, LLC), and tafluprost (ZIOPTAN manufactured by Akorn, Incorporated).

Several laser treatments are used in the treatment of glaucoma. Different laser treatments are used to treat a number of different types of glaucoma. In open angle glaucoma, laser treatment is used to reduce the intraocular pressure (TOP) by increasing outflow of aqueous fluid from the eye (laser trabeculoplasty) or to decrease the formation of aqueous fluid (cyclophotocoagulation). In narrow angle glaucoma, laser iridotomy is used to make a small hole in the iris to improve fluid outflow or iridoplasty is performed to tighten the iris and open the drainage angle.

Argon laser trabeculoplasty (ALT) is used to treat chronic open angle glaucoma. ALT was first performed with an argon laser, although lasers used today are frequency doubled YAG lasers that perform a similar function. Typically, the trabecular meshwork is targeted, treating half of the eye in a single session. If necessary, the other half is treated later. The treatment requires eye drop anesthesia. Treatment may be used in place of eye drops, but typically is used as an adjunct to continuing treatment with drops. A different type of laser therapy or surgery may be required, as the effect of ALT may wear off after a few years. Several follow-up appointments are required after treatment in order to monitor TOP and inflammation in the patient. Typically, most patients require anti-glaucoma drops in the long-term to control the IOP at the desired level.

Selective laser trabeculopalsty (SLT) is used to treat chronic open angle glaucoma. SLT is similar to ALT, but uses a gentler laser beam of larger size. In SLT, a laser is directed at the trabecular meshwork, but uses a laser with a lower power than ALT treatment. The best SLT results are produced when all 360 degrees of the trabecular meshwork is treated at once. Unlike ALT, SLT can be repeated if the effect wears off. Several follow-up appointments are required after treatment in order to monitor TOP and inflammation in the patient. Typically, most patients require anti-glaucoma drops in the long-term to control the TOP at the desired level.

Trans-scleral photocoagulation, cyclodiode or diode laser cycloablation, is used to treat chronic open angle glaucoma. A laser is used to target the ciliary body that produces the fluid. A general anesthetic or a local anesthetic injection is often required for treatment. Trans-scleral photocoagulation can be repeated if the TOP is not considered low enough or the effect wears off with time. Cyclodiode is also recommended in a number of other forms of glaucoma where very high IOPs occur and traditional surgery is contraindicated or impossible. Patients undergoing cyclodiode often require strong painkillers after the treatment. Several follow-up appointments are required after treatment in order to monitor IOP and inflammation in the patient. Typically, most patients require anti-glaucoma drops in the long-term to control the TOP at the desired level.

Laser iridotomy is used to treat closed and narrow angle glaucoma. In laser iridotomy, a small hole is made with a Yag laser in order to relieve a narrow or closed angle. The fluid passes through the hole, inducing the iris to fall back away from the drainage meshwork, and the fluid drains freely through the meshwork. Numbing eye drops are typically administered as an anesthetic. However, in some eyes the iris does not fall back as desired, thus requiring other treatments. Even with a good iris position, medication or surgery may still be required to control the TOP. Post-laser drops are required, usually in the form of steroids, and anti-glaucoma drops may be necessary temporarily or indefinitely.

Peripheral iridoplasty is used to treat closed and narrow angle glaucoma. Peripheral iridoplasty may be used when the iris has not fallen back in an eye that has undergone a laser iridotomy. An argon or frequency doubled Yag laser is applied to the outer margins of the iris to shrink the iris away from the drainage meshwork and open the drainage angle. Anesthesia other than numbing drops may be required. Post-laser drops are required, usually in the form of steroids, and anti-glaucoma drops may be necessary temporarily or indefinitely.

Several surgical treatments are available to treat glaucoma. However, surgical options are often a last resort and are reserved for late-stage glaucoma patients, after pharmaceutical and laser treatment options have proved ineffective in treating the condition.

Aqueous shunts are used to reduce the intraocular pressure (TOP) in glaucoma by draining the fluid from inside the eye to a small blister or bleb behind the eyelid. Aqueous shunts have various other names such as tube implants, glaucoma tube shunts, glaucoma drainage devices, and glaucoma drainage implants. Two types of shunts commonly used include the Ahmed Glaucoma Valve (manufactured by New World Medical, Rancho Cucamonga, Calif., USA) and the Baerveldt Glaucoma Implant (manufactured by Advanced Medical Optics, Inc., Santa Ana, Calif., USA). The shunts are made of a small silicone tube (less than 1 mm in diameter) attached to a plate. The tube takes the aqueous humor from inside the eye and drains it to the plate which sits on the white of the eye (sclera). The plate sits under the skin of the eye conjunctiva), behind the eyelid.

Trabeculectomy is a surgical procedure used to treat glaucoma and is sometimes referred to as filtration surgery. During a trabeculectomy, a physician removes a piece of tissue in the drainage angle of the eye to create an opening. The opening is partially covered with a flap of tissue from the sclera, the white part of the eye, and the conjunctiva, the clear thin covering over the sclera. The newly-created opening allows fluid to drain out of the eye, bypassing the clogged drainage channels of the trabecular meshwork. A bleb is formed when fluid flows through the new drainage opening and the tissue over the opening rises to form a little blister or bubble.

Trabeculotomy is a surgical procedure much like trabeculectomy. A physician removes a piece of tissue in the eye's drainage angle to create an opening. The newly-created opening allows fluid to drain out of the eye. Trabeculotomy surgery is for children only.

During a goniotomy, a physician uses a goniolens to see the structures of the front part of the eye, or anterior chamber. The physician makes an opening in the trabecular meshwork, the group of tiny canals located in the drainage angle where fluid leaves the eye. The newly-created opening allows fluid to flow out of the eye. Goniotomy surgery is for children only.

Deep sclerectomy is a non-penetrating surgical procedure used for treatment of open angle glaucoma. The deep sclerectomy procedure involves removing the inner wall of Schlemm's canal and juxta-canalicular trabecular meshwork, the structures responsible for most of the outflow resistance in open angle glaucoma. The aqueous outflow is enhanced, and a trabeculo-Descemet's membrane (TDM) is left intact to control aqueous outflow through the filtration site.

In viscocanalostomy, tissue flaps are cut in the conjunctiva and the sclera to expose a portion of the drainage canal (Schlemm's canal). The procedure involves production of superficial and deep scleral flaps, excision of the deep scleral flap to create a scleral reservoir, and unroofing of Schlemm's canal. A high-viscosity elastic gel is injected in Schlemm's canal to open and enlarge the canal to allow increased fluid flow out of the anterior chamber. For example, the high-viscosity viscoelastic may comprise sodium hyaluronate. The tissue flaps are then closed. For example, the superficial scleral flap may be sutured water tight, trapping the viscoelastic until healing takes place.

In the invention, previously-attempted treatment methods have proved ineffective at treating glaucoma in a patient. Methods of the invention use an excimer laser to permanently perforate the Schlemm's canal and/or trabecular meshwork to create an internal outflow channel. Such ablation with excimer lasers causes almost no thermal damage, thereby minimizing inflammation and formation of scar tissue. In contrast, because of inflammatory and healing responses, other lasers, such as ruby and argon lasers, cannot achieve a permanent perforation of the trabecular meshwork. Therefore, the invention uses ELT to reestablish outflow of fluid from the eye without inciting a healing response at the target tissue. Due to the lack of inflammation and scar tissue formation, methods of treatment of the invention require less recovery time than traditional surgical methods, such as placement of implants.

In embodiments of the invention, multiple shots from an excimer laser are administered to the patient in order to create perforations in the trabecular meshwork and/or Schlemm's canal. ELT converts trabecular meshwork tissue into gas by photoablation. By permanently perforating Schlemm's canal and/or the trabecular meshwork, built-up fluid in the eye is immediately allowed to drain. Moreover, because the perforations allow for increased outflow of aqueous humor and fluid drainage, subsequent vision loss from damage to the optic nerve due to any build-up is thereby avoided.

Figure 1:
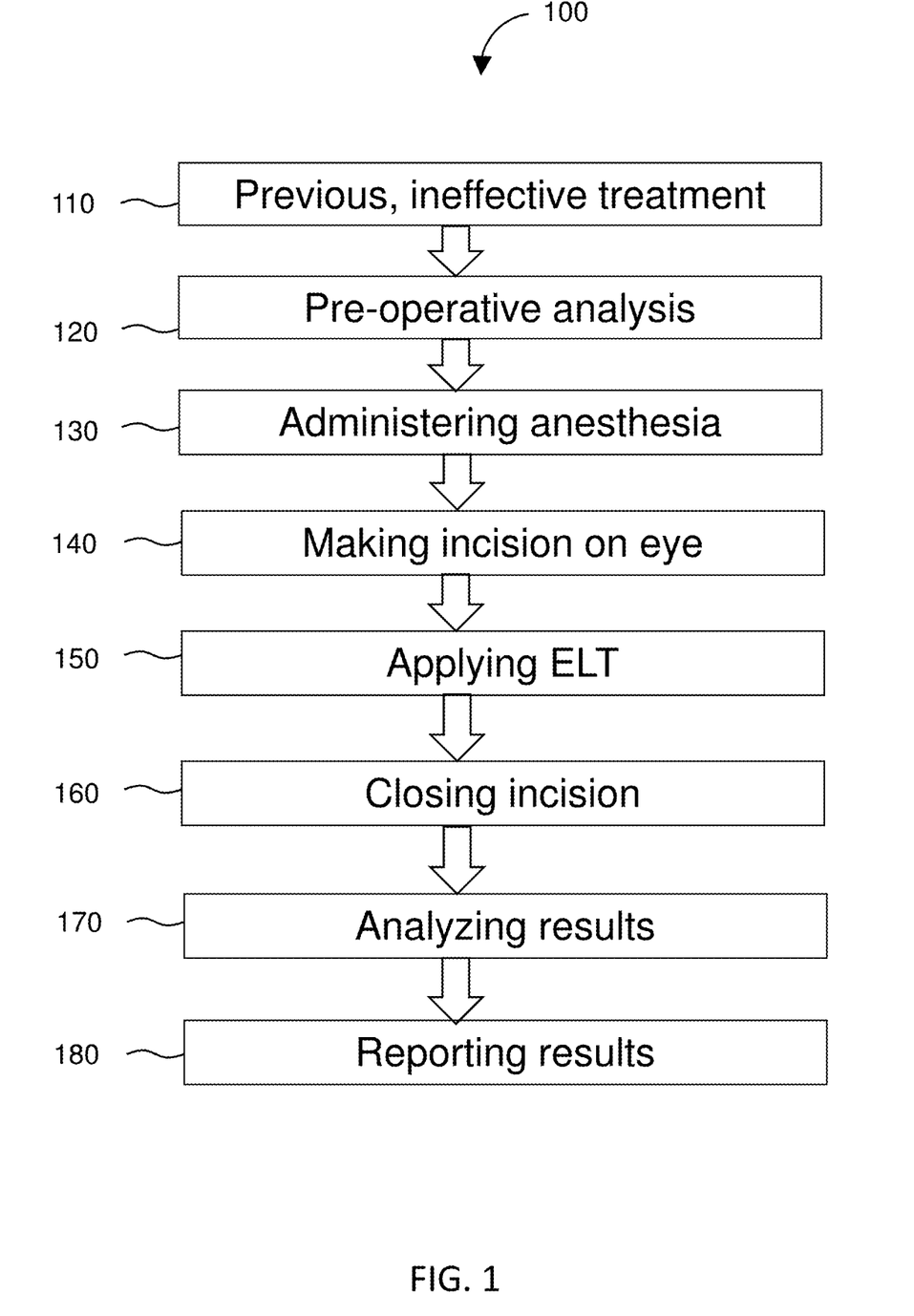
FIG. 1 is a flowchart of an embodiment of methods of the invention.

FIG. 1 shows a flowchart of an embodiment 100 of methods of the invention. Methods of the invention are directed to treating a patient having glaucoma with ELT. In the invention, the energy shots delivered from the excimer laser are at a position transverse to the Schlemm's canal. Methods of the invention are performed after a patient having glaucoma has been 110 administered previous, ineffective treatments. Treatments other than ELT include traditional pharmaceutical, laser, and surgical treatments. For instance, pharmaceutical treatment methods involve pills, eyedrops, or both. Typically, a prescribed medication or pharmaceutical treatment is a medicated eye drop, such as alpha agonists, beta blockers, carbonic anhydrase inhibitors, cholinergic agonists, prostaglandin/prostamide analogues, or combinations thereof. Examples of laser treatments include trabeculoplasty, iridotomy, iridectomy, and combinations thereof. Examples of trabeculoplasty include argon laser trabeculoplasty (ALT) and selective laser trabeculoplasty (SLT). Examples of surgical treatment include insertion of a shunt or implant, trabeculectomy, trabeculotomy, goniotomy, deep sclerectomy, viscocanalostomy, or combinations thereof.

In the invention, ELT is administered even if other treatments have been previously administered and are ineffective. For example, if a shunt was placed in a subject's eye and has since become dislodged, providing ELT treatment is still possible. The provided ELT treatment will allow drainage of the build-up of fluid in the eye by providing permanent perforation of the Schlemm's canal and/or trabecular meshwork.

Methods of the invention include 120 pre-operative analysis, such as diagnosis of the eye condition, determination of course of action based on previously-failed treatment methods, inspection and/or visualization of the anterior chamber of the eye to aid in placement of the laser probe, and analysis of number of laser shots needed for treatment. In the invention, excimer laser trabeculostomy (ELT) is used to treat glaucoma.

The method includes 130 administering anesthesia to the patient. Topical anesthesia is commonly employed, typically by the instillation of a local anesthetic such as tetracaine or lidocaine. Lidocaine and/or a longer-acting bupivacaine anesthetic may be injected into the area surrounding (peribulbar block) or behind (retrobulbar block) the eye muscle cone to more fully immobilize the extraocular muscles and minimize pain sensation. Optionally, a facial nerve block may be performed using lidocaine and bupivacaine to reduce lid squeezing. In some cases, such as for children, patients with traumatic eye injuries, and nervous or uncooperative patients and animals, general anesthesia is administered with cardiovascular monitoring. To prepare the area for surgery, proper sterile precautions must be taken, including use of antiseptics like povidone-iodine and employment of sterile drapes, gowns, and gloves. In some cases, an eye speculum is inserted to keep the eyelids open.

A physician 140 makes a small incision on the eye of the patient. Before the ELT procedure is performed, a small incision is made in the cornea of the eye to allow introduction of the laser probe. Typically, the incision is about ⅛ inch or smaller. During the ELT procedure, a physician guides the delivery tip of the fiber probe through a corneal incision in the eye and towards the trabecular meshwork. The delivery tip is guided by the physician to a position transverse to the Schlemm's canal. A Gonio lens, endoscope, and/or illumination source may be used by the physician to aid in positioning the delivery tip. By providing a laser probe at a position transverse to the Schlemm's canal, or crosswise to the Schlemm's canal, the laser is delivered to a greater amount of surface area than if the laser was in a parallel or perpendicular position to the Schlemm's canal, resulting in more perforation from fewer laser shots. Thus, arrangement of the delivery tip at a position transverse to the Schlemm's canal achieves optimal photoablation and perforation formation in the meshwork and/or Schlemm's canal for drainage of fluid. The orientation and positioning of the delivery tip is critical when creating perforations in the tissue, as achieving transverse placement of perforations in the meshwork relative to Schlemm's canal provides optimal drainage.

Once the delivery tip is at a position transverse to the Schlemm's canal, the physician 150 applies ELT treatment to the patient by delivering a series of shots of laser energy to the trabecular meshwork and/or Schlemm's canal. The physician applies pulsed photoablative energy to create ELT sites, or perforations, in the trabecular meshwork and/or Schlemm's canal. In some examples, a physician creates 10 ELT sites in an eye of the patient. In some examples, the physician creates greater than 10 ELT sites. A small amount of bloody reflux from Schlemm's canal confirms each opening. The fiber probe is removed from the eye. Notably, the TOP decreases immediately after administering the ELT procedure.

After applying ELT treatment, a physician 160 closes the incision. Typically, a physician uses sutures to close the incision. Some physicians place a suture in the incision and other physicians reserve a suture for when there is persistent leakage.

Methods of the invention include 170 analyzing post-operative results and 180 reporting results and/or scheduling a post-operative follow-up appointment with the patient after surgery. For example, the physician's analysis may include observing a small amount of bloody reflux from Schlemm's canal to confirm each opening. By observing the bloody reflux and drainage of aqueous humor, the physician is able to immediately verify the effectiveness of the laser treatment. In turn, the physician may report the results to the patient, prescribe post-operative medication, such as topical antibiotics and steroid drops, and schedule a follow-up post-operative visit with the patient. For example, topical antibiotics and steroid drops are used by the patient for 1 to 2 weeks post-operatively.

Figure 2:
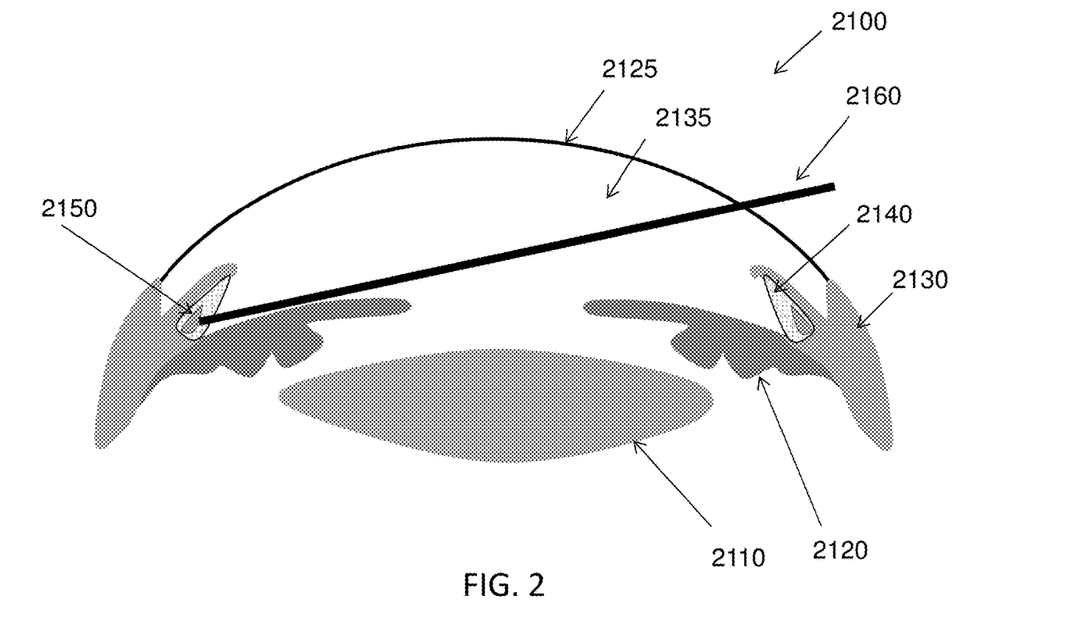
FIG. 2 is a schematic sectional view of an embodiment of the invention in an eye.
Figure 3:
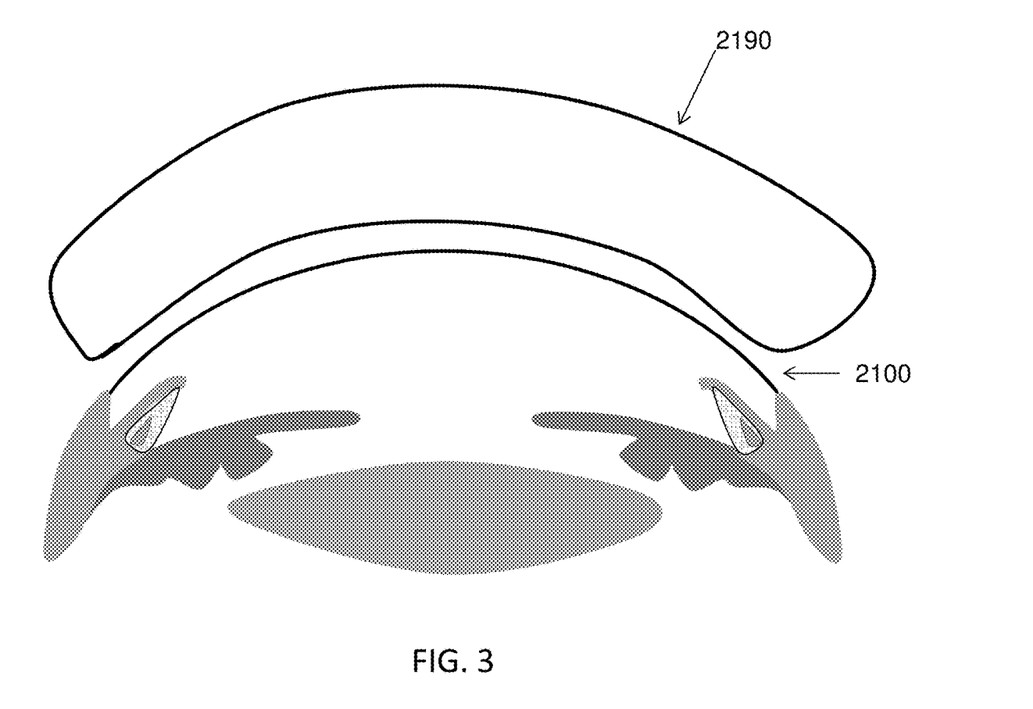
FIG. 3 shows the schematic section view of an eye with a light source aid.
Figure 4:
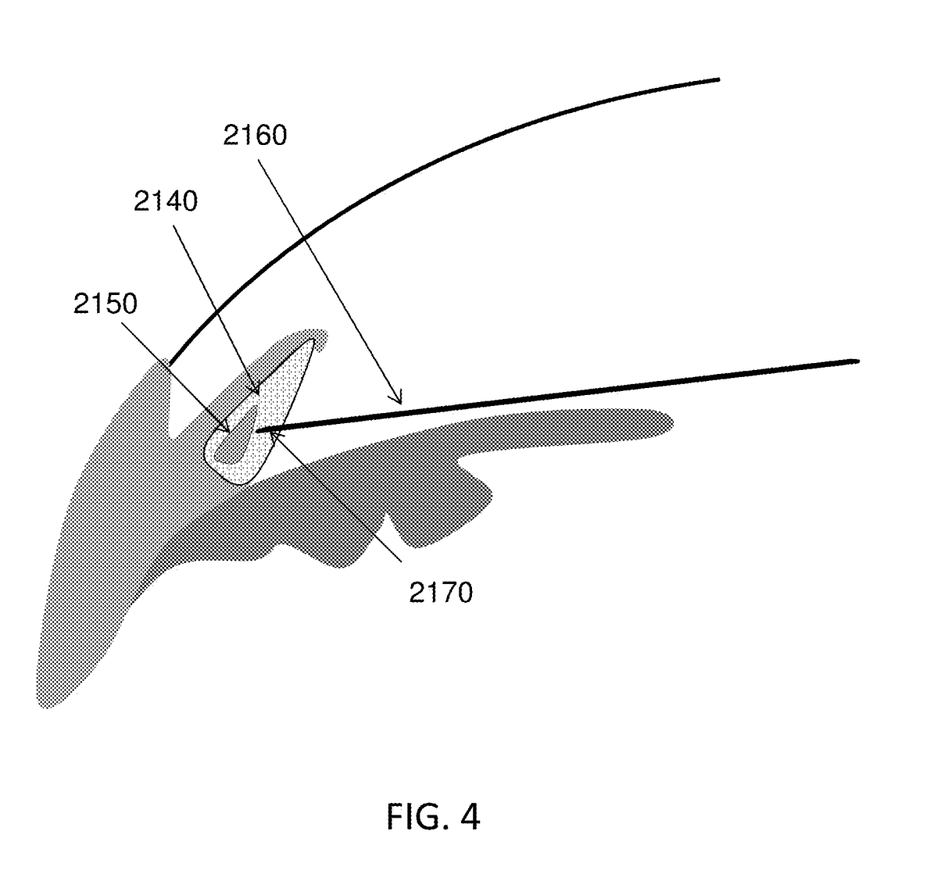
FIG. 4 is an enlarged schematic sectional view of an embodiment of the invention.

FIG. 2 is schematic sectional view of an eye 2100 illustrating the interior anatomical structure. FIG. 3 shows the schematic section view of an eye 2100 with a light source 2190, such as a Gonio lens, endoscope, or other light source. FIG. 4 is an enlarged schematic sectional view of the eye. The outer layer, or sclera, 2130 serves as a supporting framework for the eye, and the front of the outer layer 2130 includes a cornea 2125, a transparent tissue that enables light to enter the eye. An anterior chamber 2135 is located between the cornea 2125 and a crystalline lens 2110, and a posterior chamber is located behind the lens 2110. The anterior chamber 2135 contains a constantly flowing clear fluid called aqueous humor. In the anterior chamber 2135, an iris 2120 encircles the outer perimeter of the lens 2110 and includes a pupil at its center, which controls the amount of light passing through the lens 2110.

The eye further includes a trabecular meshwork 2140, which is a narrow band of spongy tissue that encircles the iris 2120 within the eye. The trabecular meshwork has a variable shape and is microscopic in size. It is of a triangular cross-section and of varying thickness in the range of 100-200 microns. It is made up of different fibrous layers having micron-sized pores forming fluid pathways for the egress of aqueous humor. The trabecular meshwork 2140 has been measured to about a thickness of about 100 microns at its anterior edge, known as Schwalbe's line, which is at the approximate juncture of the cornea and sclera.

The trabecular meshwork widens to about 200 microns at its base where it and iris 2120 attach to the scleral spur. The passageways through the pores in trabecular meshwork 2140 lead through very thin, porous tissue called the juxtacanalicular trabecular meshwork that abuts the interior side of a structure called Schlemm's canal 2150. Schlemm's canal 2150 is filled with a mixture of aqueous humor and blood components and branches off into collector channels which drain the aqueous humor into the venous system. Because aqueous humor is constantly produced by the eye, any obstruction in the trabecular meshwork, the juxtacanalicular trabecular meshwork or in Schlemm's canal prevents the aqueous humor from readily escaping from the anterior eye chamber which results in an elevation of intraocular pressure within the eye.

The eye has a drainage system for the draining aqueous humor. The aqueous humor flows from a posterior chamber behind the lens 2110 through the pupil into the anterior chamber 2135 to the trabecular meshwork 2140 and into Schlemm's canal 2150 to collector channels and then to aqueous veins. The obstruction of the aqueous humor outflow which occurs in most open angle glaucoma (i.e., glaucoma characterized by gonioscopically readily visible trabecular meshwork) typically is localized to the region of the juxtacanalicular trabecular meshwork located between the trabecular meshwork 2140 and Schlemm's canal 2150, more specifically, the inner wall of Schlemm's canal. When an obstruction develops, such as at the juxtacanalicular trabecular meshwork or at Schlemm's canal, intraocular pressure gradually increases over time, leading to damage and atrophy of the optic nerve, subsequent visual field disturbances, and eventual blindness if left untreated.

A laser probe according to the invention is used to treat glaucoma. The delivery tip of the laser probe 2160 is guided through a small incision, typically about ⅛ inch or smaller, in the cornea 2125 of the eye and across the anterior chamber 2135 to a position transverse to the Schlemm's canal 2150. The laser probe is coupled to a laser source and transmits laser energy from the laser source to the trabecular meshwork 2140 and Schlemm's canal 2150, resulting in photoablation of tissue including at least the trabecular meshwork 2140 and, in some instances, the Schlemm's canal 2150. The photoablation from the laser energy creates channels in the meshwork and Schlemm's canal, thereby improving fluid drainage into the Schlemm's canal 2150 and reducing intraocular pressure in the eye.

FIG. 4 shows the arrangement of the delivery tip 2160 at a position transverse 2170 to the Schlemm's canal 2150. Arrangement of the laser at a transverse position to the Schlemm's canal allows the laser path to travel crosswise through the trabecular meshwork to the Schlemm's canal. By positioning the laser transverse to the Schlemm's canal, the laser is able to provide photoablation to a greater amount of surface area of the trabecular meshwork in comparison to a laser arranged at positions perpendicular or parallel to the Schlemm's canal. Moreover, if the delivery tip of the laser was positioned parallel to the Schlemm's canal, the laser would not provide photoablation to any surface area of the trabecular meshwork or Schlemm's canal.

Figure 5:
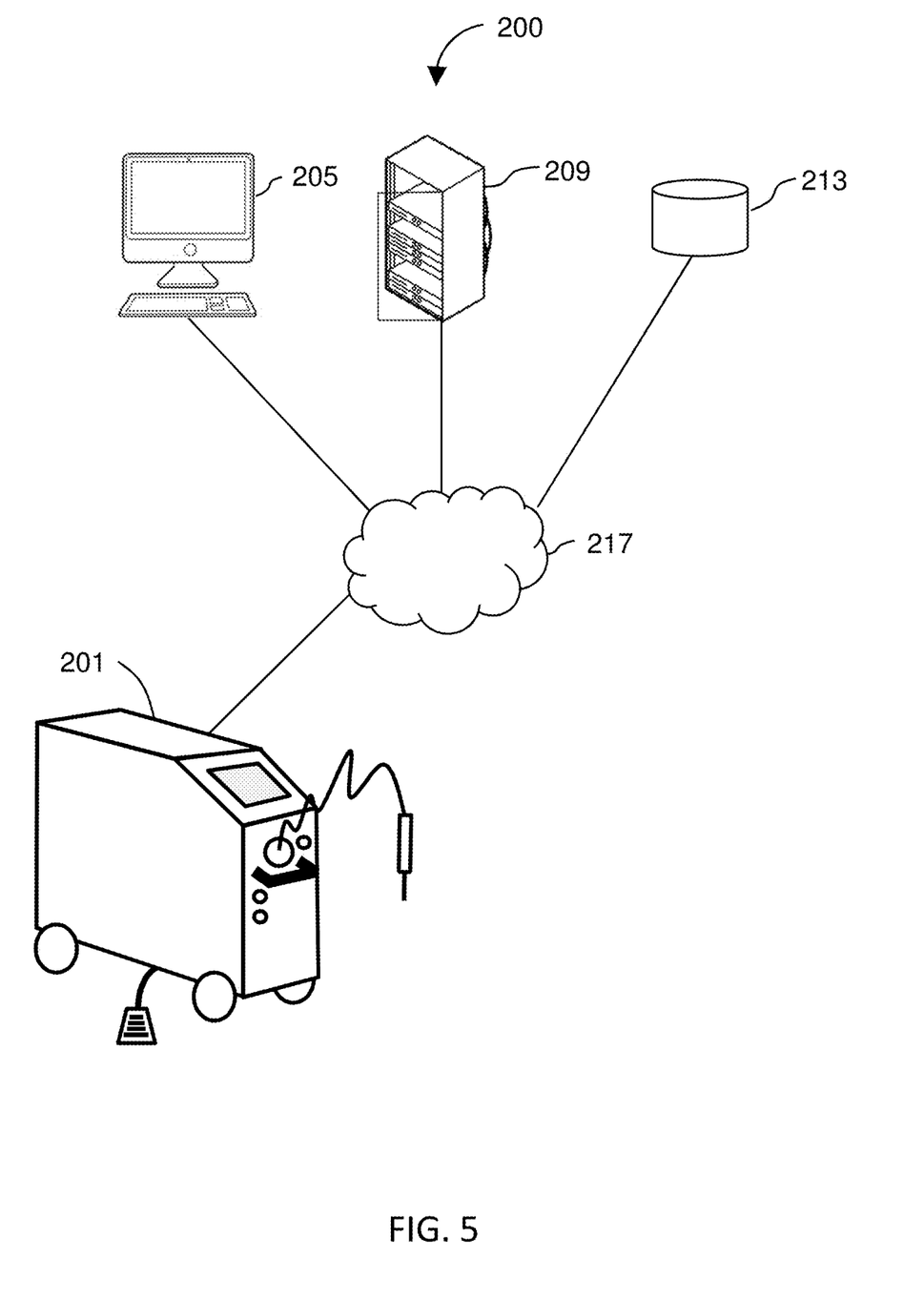
FIG. 5 shows an embodiment of systems of the invention.

FIG. 5 diagrams a schematic of system 200 according to certain embodiments of the invention. The system 200 includes an ELT instrument 201 communicatively coupled to a computer 205. The system 200 optionally includes a server 209 and storage 213. Any of the ELT instrument 201, the computer 205, the server 209, and the storage 213 that are included preferably exchange data via communication network 217. Where methods of the invention employ a client/server architecture, steps of methods of the invention may be performed using the server, which includes one or more of processors and memory, capable of obtaining data, instructions, etc., or providing results via an interface module or providing results as a file. The server may be provided by a single or multiple computer devices, such as the rack-mounted computers sold under the trademark BLADE by Hitachi. In system 200, each computer preferably includes at least one processor coupled to a memory and at least one input/output (I/O) mechanism.

A processor generally includes a chip, such as a single core or multi-core chip, to provide a central processing unit (CPU). A processor may be provided by a chip from Intel or AMD. Memory can include one or more machine-readable devices on which is stored one or more sets of instructions (e.g., software) which, when executed by the processor(s) of any one of the disclosed computers can accomplish some or all of the methodologies or functions described herein. A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem. The system 200 may be used to perform methods described herein. Instructions for any method step may be stored in memory and a processor may execute those instructions.

Figure 6:
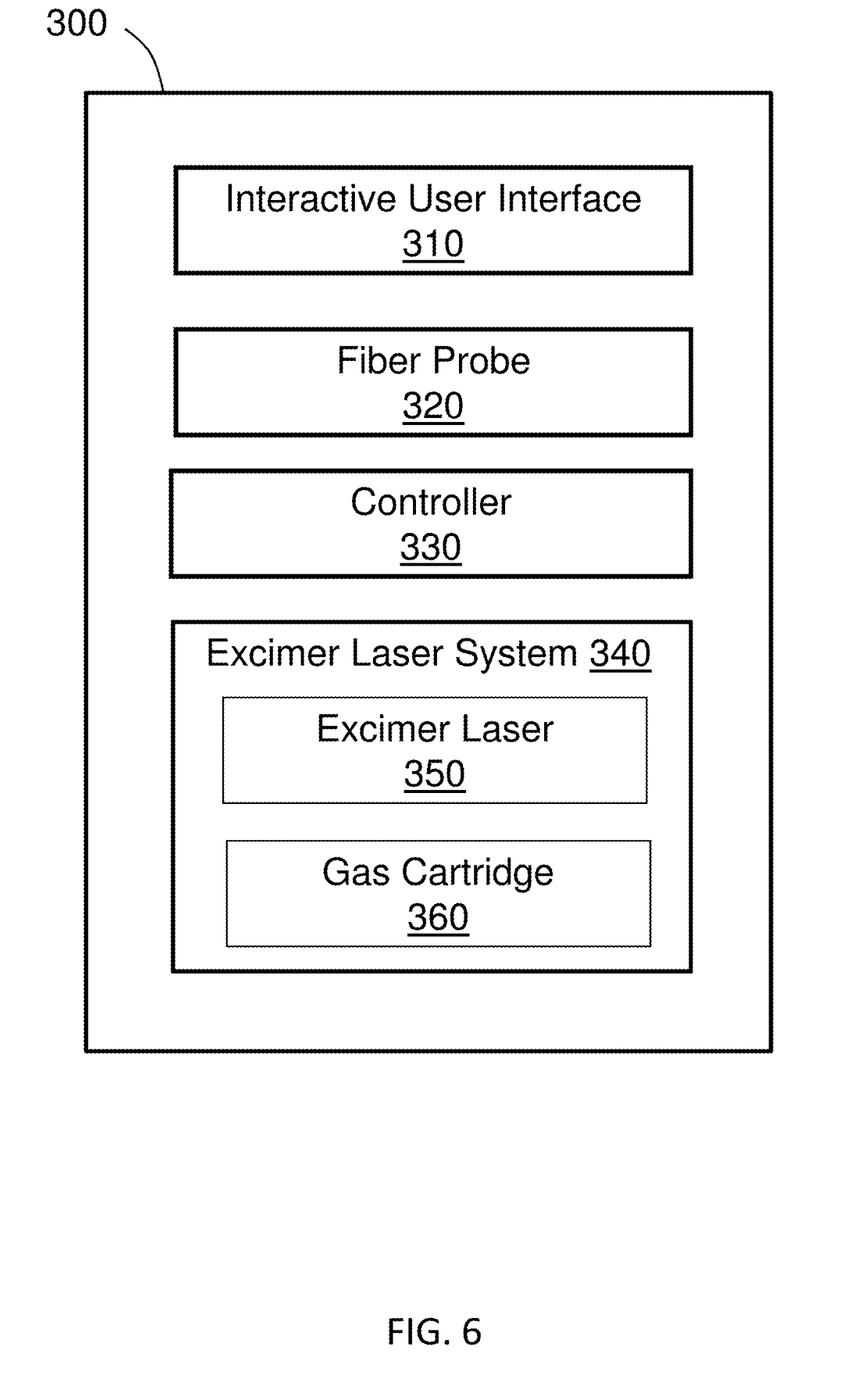
FIG. 6 shows an embodiment of systems of the invention.
Figure 9:
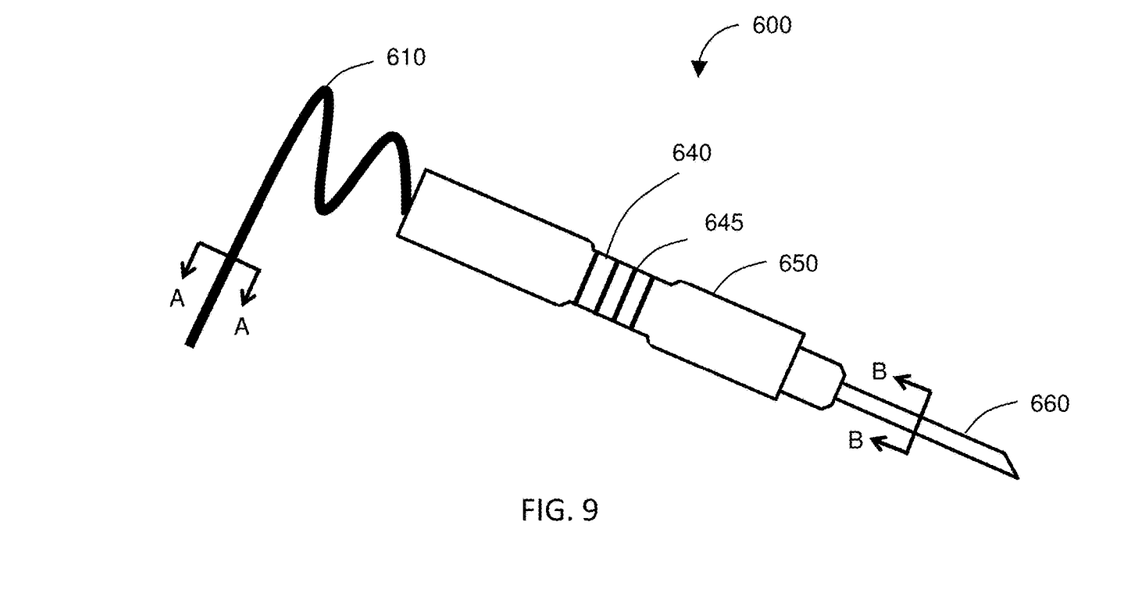
FIG. 9 shows an embodiment of a fiber probe.
Figure 10:
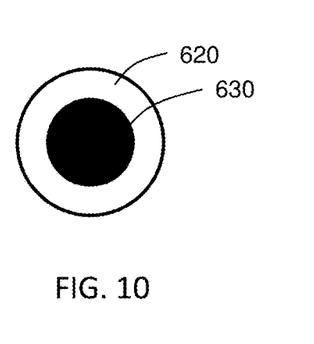
FIG. 10 shows a cross-sectional view of a fiber probe along line A-A of FIG. 9.

FIG. 6 is a diagram of a system 300 for treating glaucoma according to the invention. The treatment system 300 comprises an interactive user interface 310 (example user interface 410 shown in FIG. 8), a fiber probe 320 (examples of fiber probes 500, 600 are shown in FIGS. 9 and 10), controller 330, and an excimer laser trabeculostomy (ELT) system 340 (example ELT device 400 shown in FIG. 7). The excimer laser system 340 comprises an excimer laser 350 and gas cartridge 360. The excimer laser system 340, interactive user interface 310, and fiber probe 320 are communicatively coupled to the controller 330. Moreover, the excimer laser system 340 may be contained in a housing that includes an interactive user interface, and a fiber probe may connect to the housing for use during ELT treatment.

The controller 330 has a processor. The processor generally includes a chip, such as a single core or multi-core chip, to provide a central processing unit (CPU), such as a chip from Intel or AMD. The controller 330 provides an operator (i.e., physician, surgeon, or other medical professional) with control over the treatment system 300, including programming of the fiber probe, output of laser signals, and control over the transmission of laser energy from the laser source 350 to the fiber probe 320 that delivers the laser transmission.

The controller 330 may include software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. For example, the controller 330 may include a hardware processor coupled to non-transitory, computer-readable memory containing instructions executable by the processor to cause the controller to carry out various functions of the treatment system 300 as described herein, including controlling the laser delivery and using the interactive user interface 310 to program the number of laser shots deliverable by the fiber probe 320.

The laser system 340 includes an excimer laser 350 and a gas cartridge 360 for providing the appropriate gas combination to the laser 350. The excimer laser 350 is a form of ultraviolet laser that generally operates in the UV spectral region and generates nanosecond pulses. The excimer gain medium (i.e., the medium contained within the gas cartridge 360) is generally a gas mixture containing a noble gas (e.g., argon, krypton, or xenon) and a reactive gas (e.g., fluorine or chlorine). Under the appropriate conditions of electrical stimulation and high pressure, a pseudo-molecule called an excimer (or in the case of noble gas halides, exciplex) is created, which can only exist in an energized state and can give rise to laser light in the UV range.

Laser action in an excimer molecule occurs because it has a bound (associative) excited state, but a repulsive (dissociative) ground state. Noble gases such as xenon and krypton are highly inert and do not usually form chemical compounds. However, when in an excited state (induced by electrical discharge or high-energy electron beams), they can form temporarily bound molecules with themselves (excimer) or with halogens (exciplex) such as fluorine and chlorine. The excited compound can release its excess energy by undergoing spontaneous or stimulated emission, resulting in a strongly repulsive ground state molecule which very quickly (on the order of a picosecond) dissociates back into two unbound atoms. This forms a population inversion. The excimer laser 350 of the present system 300 is an XeCl excimer laser and emits a wavelength of 308 nm.

Figure 7:
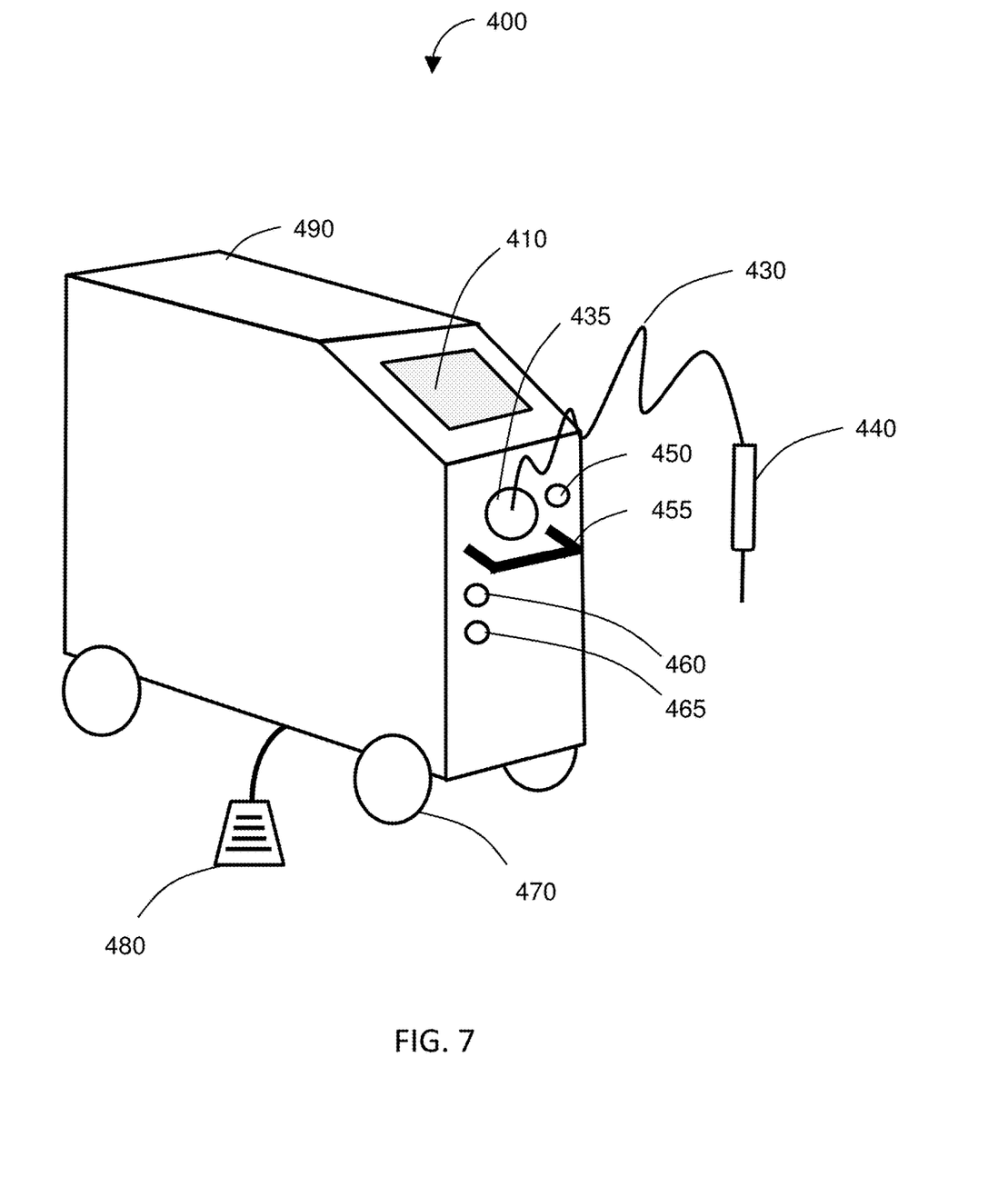
FIG. 7 shows an embodiment of an ELT system.

FIG. 7 shows an embodiment of the excimer laser trabeculostomy (ELT) instrument 400. An excimer laser is contained in the housing 490. The housing has wheels 470 and is portable. The push-pull handle 455 assists with portability of the ELT instrument 400. A foot pedal 480 extends from the housing 490 and is operable to provide power for delivering shots from the laser through the fiber probe 440. The connector 430 of the fiber probe 440 connects to the excimer laser in the housing 490 at the fiber connection port 435. The housing comprises an interactive user interface 410. In some examples, the interactive user interface 410 displays patient information, machine settings, and procedure information. The housing 490 includes control buttons, switches, and dials, such as a fiber probe cap holder 450, an emergency stop button 460, and a power switch 465.

Figure 8:
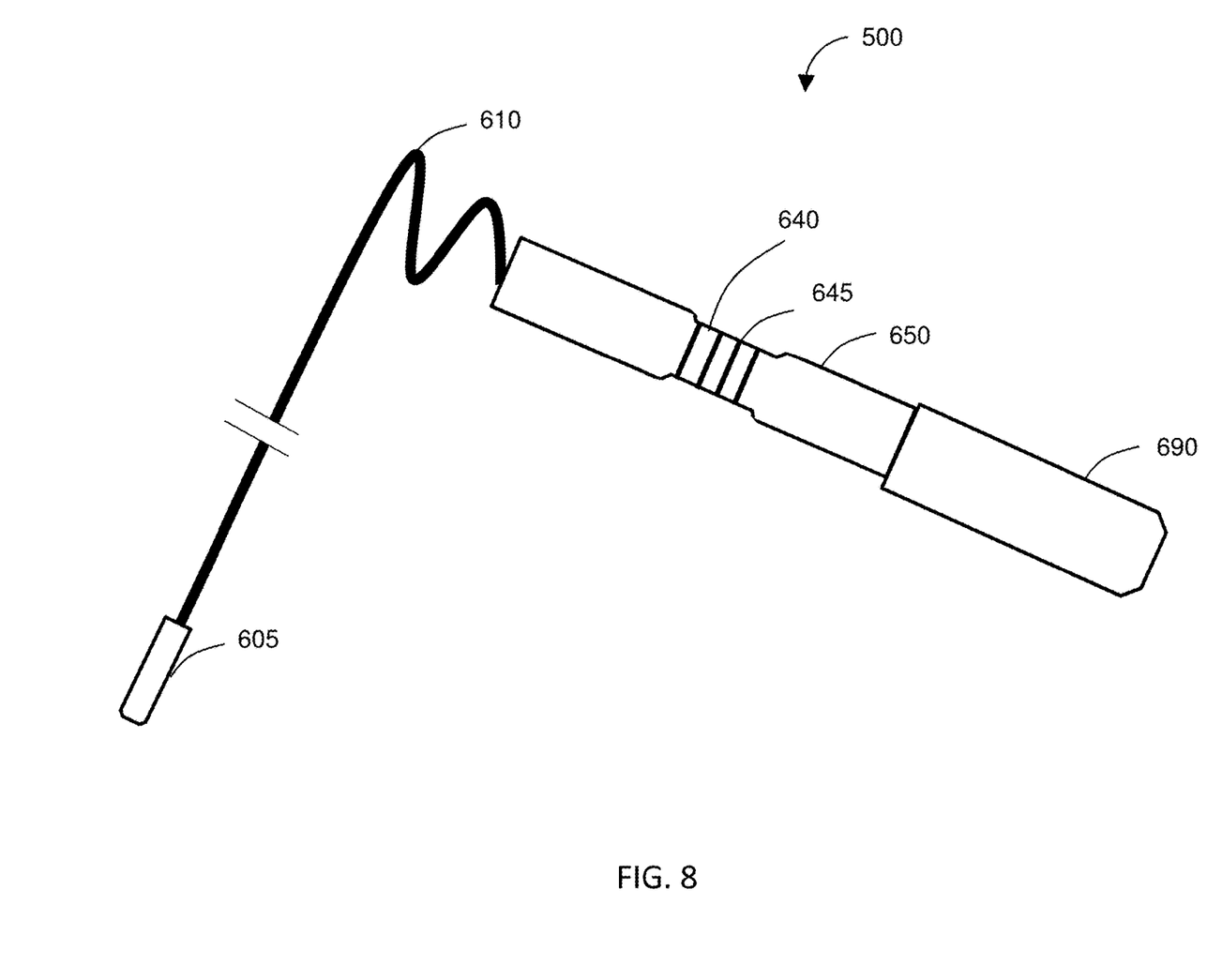
FIG. 8 shows a capped embodiment of a fiber probe.

FIG. 8 shows a capped version of the fiber probe 500. FIG. 9 shows an uncapped version of the ELT probe or fiber probe 600. The fiber probe 500, 600 comprises an optical fiber 630 that runs through the fiber probe 600 and connects the fiber probe 600 to the excimer laser. The connector 610 comprises the optical fiber 630 surrounded by a protective sheath 620. In an example, the connector 610 is about 200 cm to about 300 cm in length. A proximal end of the connector has a connection plug 605 that is operable to interact with the connection point on the instrument. In an example, the connection plug 605 has threads that match up with threads on the connection port to secure the connector 610 to the instrument. In an example, the connection plug 605 has a ridge around the plug that matches up with a slot in the connection port to secure the connector 610 to the instrument. The connector 610 connects a connection point on the instrument (such as connection port 435 shown in FIG. 7) to the body 650 of the handheld fiber probe 600.

The fiber probe 600 is sterilized by any suitable method that provides sterilized equipment suitable for use on humans. In some embodiments, the fiber probe 600 is disposable. In some embodiments, the fiber probe 600 has a tag that determines operability. In some examples, a radio frequency identification (RFID) tag must match an RFID on the instrument in order to operate. In an embodiment, the body 650 of the handheld probe is plastic. In an embodiment, the body 650 of the fiber probe 500, 600 is about 5 cm to about 10 cm in length. Preferably, the body 650 of the fiber probe is about 7 cm in length. Optionally, the body may have a finger grip 640 with ridges 645. The fiber tip 660 at the distal end of the probe comprises an optical fiber 630 jacketed in metal 670, such as stainless steel or titanium. The jacketed fiber at the distal end of the probe is inserted into the trabecular meshwork of the eye. A foot pedal is depressed to power the laser. When powered, the laser delivers a shot from the laser that travels through the optical fiber to the trabecular meshwork and Schlemm's canal.

Figure 11:
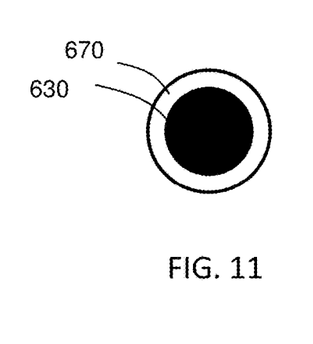
FIG. 11 shows a cross-sectional view of a fiber probe along line B-B of FIG. 9.

FIG. 10 shows a cross-sectional view of the fiber probe across line A-A of FIG. 9. The cross-section shown in A-A is the cross-section of the connector 610 from FIG. 9. A protective sheath 620 surrounds the optical fiber 630. In some examples, the protective sheath is a protective plastic or rubber sheath. FIG. 11 shows a cross-sectional view of the fiber probe across line B-B of FIG. 9. The cross-section shown in B-B is the cross-section of the fiber tip 660 from FIG. 9. A metal jacket 670 covers the optical fiber 630. In some cases, stainless steel jackets the optical fiber in the fiber tip.

INCORPORATION BY REFERENCE

References and citations to other documents, such as patents, patent applications, patent publications, journals, books, papers, and web contents made throughout this disclosure are hereby incorporated herein by reference in their entirety for all purposes.

EQUIVALENTS

While the present invention has been described in conjunction with certain embodiments, one of ordinary skill, after reading the foregoing specification, will be able to effect various changes, substitutions of equivalents, and other alterations to the compositions and methods set forth herein.

The invention claimed is:

1. A method of treating a subject having glaucoma comprising:
performing excimer laser trabeculostomy (ELT) on the subject having the glaucoma, wherein the subject has previously undergone one or more failed treatments for the glaucoma and the ELT is performed after the one or more failed treatments have been attempted with the subject, wherein the one or more failed treatments comprises at least one of a surgical eye treatment or a laser eye treatment.

2. The method of claim 1, wherein the one or more failed treatments further comprises a non-surgical treatment comprising administering medicated eye drops.

3. The method of claim 2, wherein the medicated eye drops comprise alpha agonists, beta blockers, carbonic anhydrase inhibitors, cholinergic agonists, prostaglandin/prostamide analogues, or a combination thereof.

4. The method of claim 1, wherein the one or more failed treatments is the laser eye treatment.

5. The method of claim 4, wherein the laser eye treatment comprises non-invasive laser trabeculoplasty, iridotomy, iridectomy, or a combination thereof.

6. The method of claim 5, wherein the trabeculoplasty comprises selective laser trabeculoplasty (SLT).

7. The method of claim 1, wherein the one or more failed treatments is the surgical eye treatment.

8. The method of claim 7, wherein the surgical eye treatment comprises insertion of a shunt or implant, trabeculectomy, trabeculotomy, goniotomy, deep sclerectomy, viscocanalostomy, or a combination thereof.

9. The method of claim 1, wherein performing ELT comprises:
inserting a fiber probe into an eye of the subject;
adjusting placement of the fiber probe in the eye; and
applying a plurality of shots from an excimer laser.

10. The method of claim 9, wherein the excimer laser is a xenon chloride laser.

11. The method of claim 9, wherein placement of the fiber probe is in a position transverse to Schlemm's canal in the eye.

12. The method of claim 11, wherein a light source aids in adjusting placement of the fiber probe.

13. The method of claim 12, wherein the light source is a Gonio lens, endoscope, or other illumination source.

14. The method of claim 9, further comprising administering anesthesia to the subject before inserting the fiber probe.

15. The method of claim 9, further comprising postoperative analysis comprising visualizing drainage of aqueous humor and bloody reflux flowing from Schlemm's canal in the eye.

* * * * *